United States Patent
Padyachi et al.

(10) Patent No.: US 11,185,482 B2
(45) Date of Patent: *Nov. 30, 2021

(54) ALCOHOL CONTAINING LOW-WATER CLEANSING COMPOSITION

(71) Applicant: GOJO Industries, Inc., Akron, OH (US)

(72) Inventors: Venkatesan Padyachi, Kendall Park, NJ (US); Srini Venkatesh, Hudson, OH (US); Daniel M. Willis, Clinton, OH (US); Nick E. Ciavarella, Seven Hills, OH (US); Dewain Garner, Copley, OH (US)

(73) Assignee: GOJO Industries, Inc., Akron, OH (US)

( * ) Notice: Subject to any disclaimer, the term of this patent is extended or adjusted under 35 U.S.C. 154(b) by 0 days.

This patent is subject to a terminal disclaimer.

(21) Appl. No.: 15/967,815

(22) Filed: May 1, 2018

(65) Prior Publication Data

US 2018/0311127 A1 Nov. 1, 2018

Related U.S. Application Data

(60) Provisional application No. 62/492,622, filed on May 1, 2017, provisional application No. 62/555,986, filed (Continued)

(51) Int. Cl.
*A61K 8/34* (2006.01)
*A61Q 19/10* (2006.01)
(Continued)

(52) U.S. Cl.
CPC ............ *A61K 8/34* (2013.01); *A61K 8/046* (2013.01); *A61Q 17/005* (2013.01); *A61Q 19/10* (2013.01);
(Continued)

(58) Field of Classification Search
CPC ...... A61K 8/046; A61K 8/34; A61K 2800/34; A61Q 19/10; C11D 1/02; C11D 1/88; C11D 3/2006
See application file for complete search history.

(56) References Cited

U.S. PATENT DOCUMENTS 5,851,974 A 12/1998 Sandhu
6,048,834 A 4/2000 Drapier et al.
(Continued)

FOREIGN PATENT DOCUMENTS

AU 669450 B2 6/1996
AU 2005209647 A1 10/2005
(Continued)

OTHER PUBLICATIONS

International Search Report and Written Opinion from PCT/US2018/030444 dated Jul. 25, 2018 (6 pages).
(Continued)

*Primary Examiner* — Brian P Mruk
(74) *Attorney, Agent, or Firm* — Calfee, Halter & Griswold LLP

(57) ABSTRACT

A low-water cleansing composition is provided that includes 5.0 wt. % to less than 40 wt. % of one or more $C_1$-$C_8$ alcohol, at least 10.0 wt. % of a mixture of two or more surfactants, at least 0.05 wt. % of a pH adjuster; and water, the concentrations being based on a total weight of the low-water cleansing composition.

12 Claims, 5 Drawing Sheets

Related U.S. Application Data on Sep. 8, 2017, provisional application No. 62/609,487, filed on Dec. 22, 2017.

(51) Int. Cl.
| | | |
|---|---|---|
| *C11D 1/02* | (2006.01) | |
| *C11D 1/88* | (2006.01) | |
| *A61K 8/04* | (2006.01) | |
| *A61Q 17/00* | (2006.01) | |

(52) U.S. Cl.
CPC ...... *A61K 2800/34* (2013.01); *A61K 2800/75* (2013.01)

(56) References Cited

U.S. PATENT DOCUMENTS

| | | |
|---|---|---|
| 6,269,817 B1 | 8/2001 | Nagashima et al. |
| 6,455,482 B1 | 9/2002 | D'Ambrogio et al. |
| 7,348,299 B2 | 3/2008 | Keenan et al. |
| 2004/0136943 A1 | 7/2004 | Tomokuni |
| 2005/0000394 A1 | 1/2005 | Ochs et al. |
| 2005/0003994 A1 | 1/2005 | Ochs et al. |
| 2006/0018853 A1 | 1/2006 | Watanabe |
| 2007/0066499 A1 | 3/2007 | Slavtcheff et al. |
| 2007/0219107 A1* | 9/2007 | Nonomura ............. A61K 8/556 510/280 |
| 2010/0172847 A1 | 7/2010 | Modak et al. |
| 2011/0263471 A1 | 10/2011 | Barnhart et al. |
| 2012/0295831 A1 | 11/2012 | Masters et al. |
| 2013/0172415 A1 | 7/2013 | Vermeulen et al. |
| 2013/0295032 A1 | 11/2013 | Yeung et al. |
| 2014/0024711 A1* | 1/2014 | Hedbom ............... A61K 8/463 514/556 |
| 2014/0135245 A1 | 5/2014 | Annaheim et al. |
| 2015/0250166 A1 | 9/2015 | Goldblum et al. |
| 2016/0060416 A1 | 3/2016 | Fernandez De Castro et al. |
| 2017/0216191 A1 | 8/2017 | Deisenroth et al. |
| 2017/0281497 A1* | 10/2017 | Kobayashi ............. A61K 8/44 |
| 2020/0131454 A1* | 4/2020 | Copeland ............... A61K 8/34 |
| 2021/0071107 A1 | 3/2021 | Tang et al. |

FOREIGN PATENT DOCUMENTS

| | | | |
|---|---|---|---|
| CN | 101756803 A | 6/2010 | |
| CN | 107669667 A | 2/2018 | |
| CN | 108324635 A | 7/2018 | |
| DE | 4444237 A1 | 6/1996 | |
| JP | 63054311 A | 3/1988 | |
| KR | 20100078777 A | 7/2010 | |
| WO | 2008/157847 A1 | 12/2008 | |
| WO | 2016/104692 A1 | 6/2016 | |
| WO | WO 2016/104692 * | 6/2016 | ............... A61K 8/44 |

OTHER PUBLICATIONS

International Search Report and Written Opinion from PCT/US2018/030444 dated Jul. 25, 2018 (16 pages).

International Search Report and Written Opinion from PCT/US2018/030455 dated Jul. 27, 2018 (15 pages).

MINTEL: anonymous: "Shampoo for Normal Hair," XP055655438, retrieved from www.gnpd.com, Database accession No. 1536766, Abstract, May 17, 2011.

Oh et al., "Antimicrobial activity ofethanol, glycerol monolaurate or lacticacid against Listeria monocytogenes," International Journal of Foodmicrobiology, Elsevier BV, NL, vol. 20, No. 4,Dec. 1, 1993 (Dec. 1, 1993), pp. 239-246.

\* cited by examiner

ALCOHOL CONTAINING LOW-WATER CLEANSING COMPOSITION

RELATED APPLICATIONS

The present invention claims priority to and the benefits of U.S. Provisional Patent Application Ser. No. 62/492,622 titled ALCOHOL CONTAINING TOPICAL CLEANSING COMPOSITION filed on May 1, 2017; U.S. Provisional Patent Application Ser. No. 62/555,986 titled ALCOHOL CONTAINING TOPICAL CLEANSING COMPOSITION filed Sep. 8, 2017; and U.S. Provisional Patent Application Ser. No. 62/609,487 titled ALCOHOL CONTAINING TOPICAL CLEANSING COMPOSITIONS filed Dec. 22, 2017, all of which are incorporated herein in their entirety.

BACKGROUND

Hand wash compositions are preferably formulated to provide good cleaning, good foaming, and to be mild to the skin. Hand wash compositions typically employ a surfactant system to provide cleaning and foaming functionalities. Moisturizers or other skin benefit agents may also be employed to promote overall skin health and wellness.

Alcoholic products are popular as sanitizers for the skin. However, when placed on the skin alcohol can be drying and can cause irritation. Additionally, alcohol is known to have strong de-foaming properties. Thus, when alcohol is added to a hand wash, it is typically believed that skin health, aesthetics, and foam quality may be sacrificed. Therefore, it would be beneficial to design a new cleansing composition that contains alcohol without negatively impacting the composition's skin health benefits and/or foaming ability.

Cleansing compositions with low-water content are often desirable, as they offer both environmental and cost-saving benefits. Such cleansers are manufactured with less water, thereby allowing for more product to be included in a single dispenser or storage container. Thus, more product can be shipped at a time to distributor and more product may be stored in a particular dispenser at a time. This reduces the frequency of both deliveries and product refills.

SUMMARY

Various aspects of the present inventive concepts are directed to a low-water cleansing composition comprising from 10.0 wt. % to less than 40 wt. % of one or more $C_1$-$C_8$ alcohols; at least 10.0 wt. % of at least one surfactant having an HLB value of at least 8; at least 0.05 wt. % of a pH adjuster, the above concentrations being based on the total weight of the cleansing composition. The low-water cleansing composition comprises at least 5.0% active surfactant.

In some exemplary embodiments, the one or more $C_1$-$C_8$ alcohols are selected from the group consisting of methanol, ethanol, isopropanol, butanol, pentanol, hexanol, and isomers and mixtures thereof. In some instances, the one or more $C_1$-$C_8$ alcohols may include at least one of ethanol and isopropanol, or mixtures thereof.

In some exemplary embodiments, the low-water cleansing composition includes at least 15.0 wt. % of a mixture of at least two surfactants.

In some exemplary embodiments, the low-water cleansing composition is non-antimicrobial. In other aspects, the cleansing composition is an antimicrobial composition that includes 0.05 to 3.0 wt. % of an antimicrobial agent.

In some exemplary embodiments, the mixture of surfactants includes at least one anionic surfactant selected from the group consisting of sodium alkyl sulfate, sodium dodecyl sulfate, sodium dodecylbenzene sulfonate, sodium laurate, sodium laureth sulfate, sodium lauryl sarcosinate, potassium lauryl sulfate, ammonium lauryl sulfate, ammonium laureth sulfate, ammonium xylene sulfonate, magnesium laureth sulfate, and sodium myreth sulfate, sodium nonanoyloxybenzenesulfonate, carboxylates, sulphated esters, sulphated alkanolamides, alkylphenols, and mixtures thereof. The mixture of surfactants may comprise about 10.0 wt. % to about 25.0 wt. % of at least one primary surfactant and about 2.0 wt. % to about 20 wt. % of at least one secondary surfactant, based on the total weight of the cleansing composition. The primary and secondary surfactants may be included in an amount to provide a total surfactant concentration 5.0 to 20.0 wt. % active surfactant.

In some exemplary embodiments, the at least one surfactant comprising at least one zwitteronic surfactant selected from the group consisting of betaines, sultaines, amphoacetates, and amphodiacetates.

In some exemplary embodiments, the surfactant comprises a primary surfactant, which is an anionic surfactant and a secondary surfactant, which is a zwitterionic surfactant.

In some exemplary embodiments, the low-water composition is in the form of a foamable solution. The foamable solution produces a foam having a foam volume that is at least 30% greater than the foam volume of an otherwise identical low-water cleansing composition that does not include the claimed concentration of alcohol.

Further aspects of the present inventive concepts are directed to a method of cleansing a surface comprising: applying a low-water cleansing composition to a surface. The composition includes from about 5.0 wt. % to less than 40 wt. % of one or more $C_1$-$C_8$ alcohols; about 5.0 wt. % to about 25.0 wt. % of at least one anionic primary surfactant; 0 wt. % to about 20.0 wt. % of at least one secondary surfactant; and a pH adjusting agent, wherein the primary and secondary surfactants have an HLB value greater than 8 and are included in a total surfactant concentration greater than 10 wt. %. The above concentrations are based on a total weight of the low-water cleansing composition. The low-water cleansing composition comprises an active surfactant concentration of at least 5.0 wt. %.

Yet further aspects of the present inventive concepts are directed to a low-water foamable composition comprising 5.0 wt. % to less than 40 wt. % of one or more $C_1$-$C_8$ alcohol; at least 10.0 wt. % of a mixture of at least a primary and secondary surfactant; at least 0.05 wt. % of a pH adjuster; less than 3.0 wt. % of an oil; and water, the concentrations being based on a total weight of the low-water foamable composition. The foamable cleansing composition has a viscosity of 40 cPs or below.

Yet further aspects of the present inventive concepts are directed to a low-water foamable cleansing composition comprising from about 10.0 wt. % to less than 40 wt. % of one or more $C_1$-$C_8$ alcohols based on the total weight of the composition; about 5.0 wt. % to about 25.0 wt. % active surfactant of a mixture of at least two surfactants; about 0.5 wt. % to about 5.0 wt. % of at least one humectant, based on the total weight of the composition; water.

Numerous other aspects, advantages, and/or features of the general inventive concepts will become more readily apparent from the following detailed description of exemplary embodiments and from the accompanying drawings being submitted herewith.

DETAILED DESCRIPTION

Figure 1:
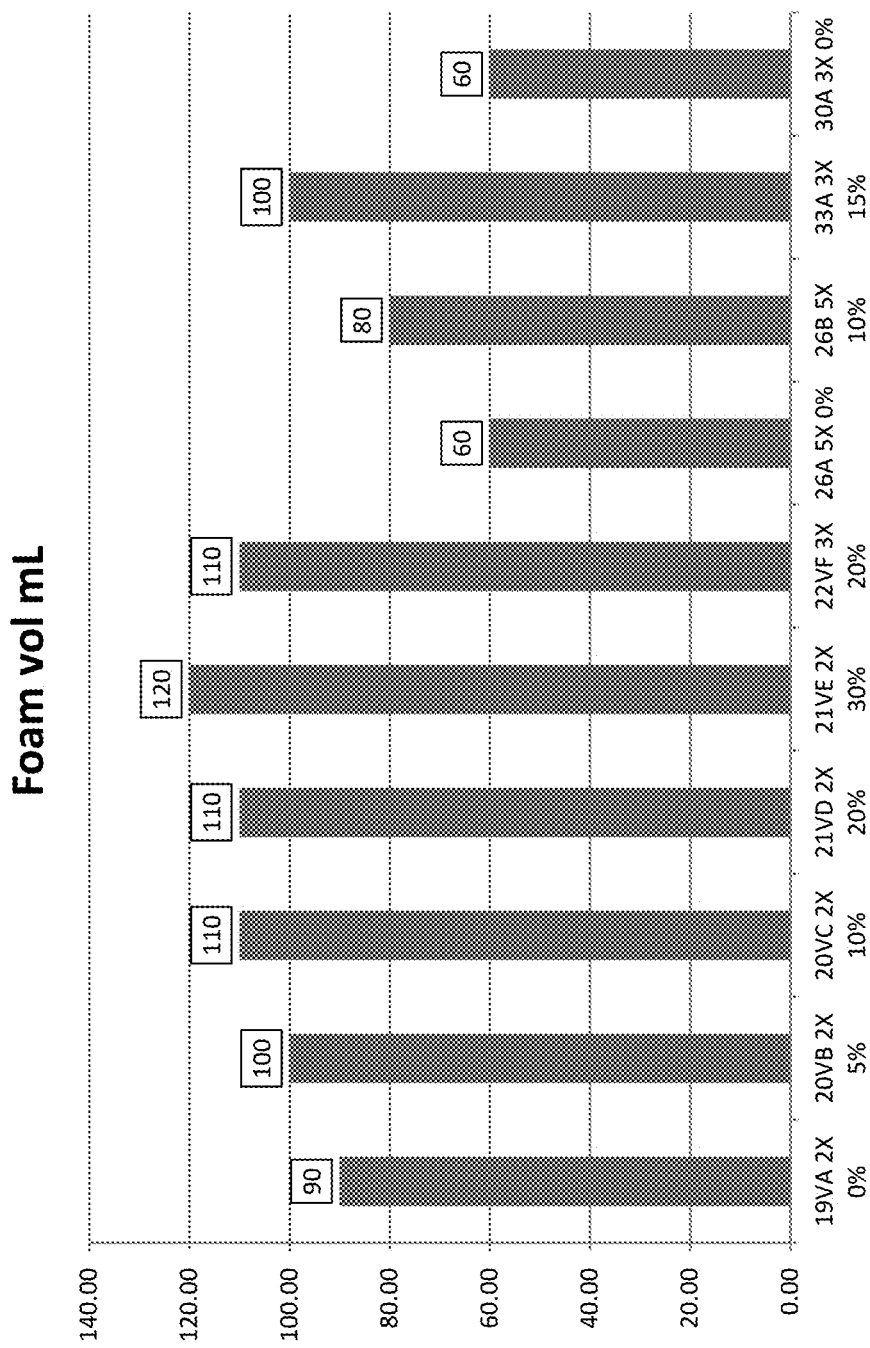
FIG. 1 graphically illustrates the foam volume in milliliters produced by various low-water cleansing compositions.

Unless otherwise defined, all technical and scientific terms used herein have the same meaning as commonly understood by one of ordinary skill in the art to which this application pertains. Although other methods and materials similar or equivalent to those described herein may be used in the practice or testing of the exemplary embodiments, exemplary suitable methods and materials are described below. In case of conflict, the present specification, including definitions, will control. In addition, the materials, methods, and examples are illustrative only and are not intended to be limiting of the general inventive concepts.

The terminology as set forth herein is for description of the exemplary embodiments only and should not be construed as limiting the application as a whole. Unless otherwise specified, "a," "an," "the," and "at least one" are used interchangeably. Furthermore, as used in the description of the application and the appended claims, the singular forms "a," "an," and "the" are inclusive of their plural forms, unless contradicted by the surrounding context.

Unless otherwise indicated, all numbers expressing quantities of ingredients, chemical and molecular properties, reaction conditions, and so forth used in the specification and claims are to be understood as being modified in all instances by the term "about." The term "about" means within +/−10% of a value, or more preferably, within +/−5% of a value, and most preferably within +/−1% of a value.

Accordingly, unless indicated to the contrary, the numerical parameters set forth in the specification and attached claims are approximations that may vary depending upon the desired properties sought to be obtained by the present exemplary embodiments. At the very least each numerical parameter should be construed in light of the number of significant digits and ordinary rounding approaches.

Every numerical range given throughout this specification and claims will include every narrower numerical range that falls within such broader numerical range, as if such narrower numerical ranges were all expressly written herein.

The phrase "topical composition" means a composition suitable for application directly to a surface, such as the surface of a human or animal body, including skin, and/or other surfaces, such as hair and nails. The topical composition may further be applied to an inanimate surface, such as a table, counter, floor, food, utensil, appliance, object, and the like.

The term "antimicrobial composition" means a composition that is able to reduce, kill, or inhibit the growth of microbes during use. Thus, an antimicrobial composition achieves an in-use antimicrobial reduction. The term "non-antimicrobial composition" includes non-antibacterial compositions, antiviral compositions, antifungal compositions and non-antiparasitic compositions. In accordance with the present inventive concepts, as defined herein, a non-antimicrobial composition achieves an antimicrobial log reduction no greater than 2.5, including no greater than 2.0, no greater than 1.5, and no greater than 1.0 log. In some exemplary embodiments, the non-antimicrobial composition achieves an antimicrobial log reduction of less than 1.0.

It has now been discovered that it is possible to formulate a low-water cleansing composition that has a proper balance of ingredients for providing a high cleansing ability, high foam, and good skin conditioning, while including alcohol.

Accordingly, the present disclosure relates to a low-water cleansing composition that includes at least one $C_1$-$C_8$ alcohol and a method of using the same. Conventionally, it was believed that the addition of alcohol to a soap composition would negatively impact skin health and reduce the foam quality of the soap. However, it has been discovered that incorporating at least one $C_1$-$C_8$ alcohol in the cleansing composition disclosed herein, provides numerous benefits to the cleansing composition, such as superior efficacy, clean release functionality, and self-preservation, while maintaining good skin health benefits and foam quality. The concept of "clean release" encompasses the ability to achieve better pathogen and soil removal on both healthy and dry/irritated skin, due at least in part to the composition's improved spreadability and wettability. The clean release functionality also provides for a faster rinse, which in turn conserves water compared to traditional commercial soap.

Additionally, various embodiments of the low-water cleansing composition are substantially free of harsh preservatives, parabens, phthalates, antimicrobial, and antibacterial ingredients. In some exemplary embodiments, the low-water cleansing composition includes less than 2.0 wt. %, less than 1.0 wt. %, less than 0.5 wt. %, or less than 0.1 wt. % of harsh preservatives, parabens, phthalates, antimicrobial, and antibacterial ingredients. In some exemplary embodiments, the low-water cleansing composition is devoid of such ingredients. In various exemplary embodiments, the low-water cleansing composition comprises at least 75% bio-based ingredients, or at least 85% bio-based ingredients, or at least 90% bio-based ingredients. In certain exemplary embodiments, the low-water cleansing composition is used for application to the skin and may be in the form of a liquid or foamable skin cleansing composition, a wipe, a concentrate, and other forms desirable for a cleansing composition. The low-water cleansing composition may be applied to the skin before, during, or after skin cleaning.

By formulating the topical cleansing composition as a "low-water" cleansing composition, the composition includes less water than a traditional cleansing composition/soap formulation. The low-water cleansing composition may be formulated as a foamable cleansing composition, a liquid cleansing composition, a gel cleansing composition, a lotion cleansing composition, or any other desirable form.

In the case of foamable compositions, water concentrations less than 90% can be considered "low-water." Generally, low-water compositions are defined by the total concentration of surfactants in the soap. If the total surfactant concentrations are greater than 5% (on 100% active solid basis), the energy required to dispense of the composition through conventional soap dispensers will increase, which is disadvantageous for offering products through conventional dispensing delivery systems, particularly those that are powered by one or more batteries. Additionally, high surfactant levels traditionally create undesirable foam aesthetics.

However, the inventive low-water cleansing composition is capable of delivering high surfactant low-water compositions (at least 5.0 wt. % active surfactant, such as greater than 10 wt. % active surfactant) through conventional dispensers. These compositions produce more foam volume and dispense with less energy usage due to the presence of alcohols and appropriate concentrations of surfactants.

Formulating a cleansing composition with reduced water provides a number of benefits, such as the ability to package the cleansing compositions in the same sized packaging as conventional diluted soap formulations, thereby delivering a higher volume of end-use cleansing composition dispenses or applications per package. In some embodiments, this increases the number of uses (applications) per bottle of soap or cleansing composition to greater than 2 times that of standard soaps or cleansing compositions, which result in sustainable benefits such as a reduction of the number of dispensing bottles and a reduction in water used for these products by >50%. For instance, an exemplary 1.2 liter container of the "low-water" cleansing composition provides about 2,400 pumps per container, while a traditional cleanser may provide about 1,200 pumps. The low-water cleansing composition also includes a high percentage of alcohol, which helps to preserve the composition and provide a longer shelf-life. In addition, alcohol helps reduce the foam dispensing energy due to reduction of surface tension and increases the compositions ability to mix with air to form foam. In certain embodiments, the low-water cleansing compositions can deliver greater than 3 times the number of pumps per volume when compared to the same volume of conventional foam cleansing compositions.

Additionally, conventional concentrated soaps are generally not used without first diluting the composition at the dispensers. For instance, U.S. 2005/0233915 discloses that the concentrated forms of the composition are diluted either at the point of sale or at the point of use. In contrast, the present low-water composition can achieve the desired foam volume and aesthetics, as dispensed, without being diluted with added water. Thus, the composition is capable of achieving a desirable foam quality and volume upon dispensing, as-is.

Surprisingly, although alcohol is generally known to be a defoamer, it has been found that alcohol concentrations in the inventive cleansing composition of up to 40 wt. % demonstrate an increased foam volume and stability. More particularly, it was unexpected to achieve a foamable low-water cleansing composition having up to 40 wt. % alcohol that does not require dilution with added water prior to use in order to produce and maintain a quality foam.

In some exemplary embodiments, the low-water cleansing composition achieves and maintains a quality foam without inclusion of traditional foam stabilizers.

The low-water cleansing composition may be provided as an aqueous solution or emulsion. In some exemplary embodiments, the cleansing composition is a single-phase solution, meaning that it is free of additional phases, such as an oil phase.

The low-water cleansing composition of the present disclosure include at least 5.0 wt. % of one or more $C_1$-$C_8$ alcohols, based on the total weight of the composition, including without limitation, at least 10.0 wt. %, or at least 15.0 wt. %, or at least 18.0 wt. %, or at least 19.0 wt. % or at least 20.0 wt. %. In some exemplary embodiments, the low-water cleansing composition includes no greater or less than 40.0 wt. % of a $C_1$-$C_8$ alcohol, based on the total weight of the low-water cleansing composition, including, without limitation, no greater than 35.0 wt. %, or no greater than 30.0 wt. %, or no greater than 28.0 wt. %, or no greater than 25.0 wt. %, or no greater than 22.0 wt. %. In some exemplary embodiments, the low-water cleansing composition includes from about 10.0 wt. % to about 40 wt. % of one or more $C_1$-$C_8$ alcohols, based on the total weight of the composition, including without limitation, about 12.0 wt. % to about 30.0 wt. %, about 15.0 wt. % to about 28.0 wt. %, about 18.0 wt. % to about 25.0 wt. %, about 18.0 wt. % to about 22.0 wt. %, about 19.0 wt. % to about 21 wt. %, and every narrower numerical range that falls within the broader ranges.

The alcohol is a $C_1$-$C_8$ alcohol, i.e. an alcohol containing 1 to 8 carbon atoms. Such alcohols may be referred to as lower alkanols. Examples of lower alkanols include, but are not limited to, methanol, ethanol, propanol, butanol, pentanol, hexanol, heptanol, and octanol and isomers and mixtures thereof. In one or more embodiments, the alcohol comprises ethanol, propanol, or butanol, or isomers or mixtures thereof. In one or more embodiments, the alcohol comprises isopropanol. In other embodiments, the alcohol comprises ethanol. In one or more embodiments, the low-water cleansing composition comprises a mixture of alcohols. In one or more embodiments, the low-water cleansing composition comprises a mixture of ethanol and isopropanol. In one or more embodiments, the low-water cleansing composition comprises a mixture of isopropanol and n-propanol.

In some exemplary embodiments, the alcohol component may be substituted by any hydrotrope capable of providing a function similar to a $C_1$-$C_8$ alcohol. Suitable hydrotropes include, for example, $C_2$-$C_8$ hydrotropes, such as $C_2$-$C_6$ diols and glycols including butylene glycol, propylene glycol, ethylene glycol, and other such diols and glycols. In various exemplary embodiments, the non-antimicrobial composition includes a mixture of an alcohol and one or more hydrotropes.

Although ethanol and other $C_1$-$C_8$ alcohols are traditionally understood to inhibit a composition's ability to foam, it has been discovered that a particular concentration of alcohol boosts rather than lowers the foaming ability of the compositions disclosed herein. In certain embodiments, the $C_1$-$C_8$ alcohol boosts the low-water cleansing composition cleansing composition foam volumes by greater than 30%, including greater than 35%, greater than 40%, and greater than 45%. The addition of alcohol to the low-water cleansing composition increases the foam volume, particularly at higher concentrations of surfactant, due to a decrease in dielectric constant of the medium (water/alcohol), a decrease of surface tension, and an increase of surfactant micelles stability. This phenomenon unexpectedly occurs at certain ratios of surfactants-to-alcohol concentrations. It has been discovered that the addition of alcohol greater than the amounts disclosed herein has the opposite effect, and negatively impacts the ability of the low-water cleansing composition to foam. Accordingly, the particular alcohol-to-surfactant ratios provided herein define an unexpected window of workability and foam improvement that is not seen outside these ranges.

The low-water cleansing composition includes water in a quantity sufficient to achieve 100% wt. % solution ("q.s."). In some exemplary embodiments, the low-water cleansing composition includes no greater than 90.0 wt. % water. In certain exemplary embodiments, the low-water cleansing composition comprises no greater than 85 wt. % water, or no greater than 75 wt. % water, or no greater than 65 wt. % water, or no greater than 45 wt. % water. In certain exemplary embodiments, the low-water cleansing composition includes at least about 1.0 wt. % water, in another embodiment the low-water cleansing composition comprises at least about 10.0 wt. % water, in another embodiment, the low-water cleansing composition comprises at least about 15.0 wt. % water, in another embodiment, the low-water cleansing composition comprises at least about 20.0 wt. % water, in another embodiment, the low-water cleansing composition comprises at least about 25.0 wt. % water. In other exemplary embodiments, the low-water cleansing composition comprises from about 10.0 wt. % to about 80.0 wt. % water, or from about 20 to 65 wt. % water. More or less water may be required in certain instances, depending particularly on other ingredients and/or the amounts thereof employed in the low-water cleansing composition.

The low-water cleansing composition cleansing composition includes a surfactant system comprising one or more surfactants present in a synergistic relationship with alcohol in amounts ranging up to about 60.0 wt. %. In some exemplary embodiment, this synergistic relationship exists when the surfactant to alcohol ratio is about 1:1 to about 1:3. In any event, the low-water cleansing composition includes at least 5.0 wt. % active surfactant, or at least 10 wt. % active surfactant. In some exemplary embodiments, the total surfactant concentration is greater than 10 wt. %, including at least 13 wt. %, at least 15 wt. %, and at least 18 wt. % surfactant, based on the total weight of the cleansing composition.

In some exemplary embodiments, the low-water cleansing composition comprises no greater than 60 wt. % total surfactants, based on the total weight of the composition. In some exemplary embodiments, the low-water cleansing composition comprises about 10.0 wt. % to about 40.0 wt. % of one or more surfactants, or about 13.0 wt. % to about 30.0 wt. % of one or more surfactants, or about 15.0 wt. % to about 25.0 wt. % of one or more surfactants. The above ranges include every narrower numerical range that falls within the broader ranges.

The surfactant system may include a combination of one or more surfactants, such as one or more anionic, cationic, nonionic, and/or zwitterionic surfactants.

The novel surfactant system boosts soap performance and works synergistically with the alcohol to provide "clean-release" functionality. As mentioned above, clean release functionality allows the soap to penetrate deeper into skin's cracks and crevices to gently remove more pathogens and soil than otherwise comparable soap that does not include the synergistic alcohol and surfactant system. This is particularly useful for dry/irritated skin, where cracks and cervices are more prevalent. In some exemplary embodiments, the clean-release functionality provided by the surfactant system removes at least 10% more soil and pathogens than traditional foam soap, excluding the synergistic alcohol and surfactant system, including at least 15%, at least 20%, at least 25%, and at least 30% more soil and pathogens than otherwise comparable soap that does not include the synergistic alcohol and surfactant system.

In some exemplary embodiments, the low-water cleansing composition comprises a combination of at least two surfactants, such as at least one primary surfactant and at least one secondary surfactant. The primary surfactant may comprise one or more anionic surfactants. The at least one primary surfactant may be present in an amount no greater than 40 wt. %, based on the total weight of the low-water cleansing composition. In some exemplary embodiments, the primary surfactant is included in an amount from about 5.0 wt. % to about 25.0 wt. %, or about 8.0 wt. % to about 20.0 wt. %, or about 10.0 wt. % to about 18.0 wt. %, based on the total weight of the low-water cleansing composition.

Exemplary anionic surfactants include sulfates, such as sodium alkyl sulfate, sodium dodecyl sulfate, sodium dodecylbenzene sulfonate, sodium laurate, sodium laureth sulfate, sodium lauryl sarcosinate, potassium lauryl sulfate, ammonium lauryl sulfate, ammonium laureth sulfate, ammonium xylene sulfonate, magnesium laureth sulfate, and sodium myreth sulfate; sulfonates, such as sodium nonanoyloxybenzenesulfonate; carboxylates; sulphated esters; sulphated alkanolamides; alkylphenols; and mixtures thereof. In some exemplary embodiments, the primary surfactant comprises any one or more of sodium laureth sulfate, ammonium lauryl sulfate, ammonium laureth sulfate, ammonium xylene sulfonate. In some exemplary embodiments, the low-water cleansing composition is free of anionic surfactants.

In some exemplary embodiments, the low-water cleansing composition comprises at least one secondary surfactant. If present, the secondary surfactant may be included in an amount no greater than about 25 wt. %, based on the total weight of the low-water cleansing composition. In some exemplary embodiments, the secondary surfactant is included in an amount from about 2.0 wt. % to about 20.0 wt. %, or about 5.0 wt. % to about 18.0 wt. %, or about 8.0 wt. % to about 15.0 wt. %, based on the total weight of the low-water cleansing composition.

In some exemplary embodiments, the low-water cleansing composition includes one or more secondary surfactants and is free of primary surfactants. In such embodiments, the total secondary surfactant concentration may reach as high as 40 wt. %.

The secondary surfactant may comprise any of zwitterionic, cationic, nonionic, or additional anionic surfactants, or mixtures thereof. Zwitterionic (amphoteric) surfactants have both cationic and anionic centers attached to the same molecule. Zwitterionic may be either anionic, cationic or no-ionic depending on the pH level of the aqueous solution. In some exemplary embodiments, the secondary surfactant includes at least one zwitterionic surfactant, or at least two zwitterionic surfactants.

Exemplary zwitterionic surfactants include betaines, such as cocomidopropyl betaine; sultaines, such as cocamidopropyl hydroxyl sultaine and lauramidopropyl hydroxyl sultaine; and amphoacetates and amphodiacetates, such as disodium lauroamphodiacetate, disodium cocoamphodiacetate, sodium lauroamphoacetate, sodium cocoamphoacetate, disodium cocoamphodipropionate and disodium lauroamphodipropionate. In some exemplary embodiments, the zwitterionic surfactant is cocamide monoethananolamine.

Exemplary nonionic surfactants include fatty alcohols such as cetyl alcohol, stearyl alcohol, cetostearyl alcohol, and oleyl alcohol, ethoxylated fatty alcohols, such as PEG-80 sorbitan laurate, polyoxyethylene glycol alkyl ethers, such as octaethylene glycol monododecyl ether, and pentaethylene glycol monododecyl ether, polyoxypropylene glycol alkyl ethers, glucoside alkyl ethers, polyoxyethylene glycol octylphenol ethers, polyoxyethylene glycol alkylphenol ethers, such as nonoxynol-9, glycerol alkyl esters such as glyceryl laurate, polyoxyethylene glycol sorbitan alkyl esters, such as polysorbate, sorbitan alkyl esters, cocamide MEA, cocamide DEA, amine oxides, such as dodecyl dimethylamine oxide, block copolymers of polyethylene glycol and polypropylene glycol, such as poloxamers, polyethoxylated tallow amine, and mixtures thereof.

Exemplary cationic surfactants include quaternary ammonium salts, linear alkyl-amines, and alkyl ammoniums.

Auxiliary surfactants may be included in the low-water cleansing composition for the purpose of boosting or modifying the foam quality and characteristics, for modifying the feel of the final formulation during rub in and/or dry time, for providing persistence or long-lasting microbial action of the alcohol, for solubilizing other ingredients such as fragrances or sunscreens, and for irritation mitigation. Auxiliary surfactants include, but are not necessarily limited to, sulfosuccinates, amine oxides, polyglucosides, alkanolamides, sorbitan derivatives, fatty alcohol ethoxylates, quaternary ammonium compounds, amidoamines, sultaines, isothionates, sarcosinates, betaines, and fatty alcohol polyethylene glycols.

As individual surfactant components may be diluted in water, the percent active surfactant in a particular composition may vary depending on the particular dilution used. For instance, the surfactants may be diluted with water prior to incorporation into the composition, to levels of 25% active surfactant, 35% active surfactant, 50% active surfactant, or 70% active surfactant, for example. Accordingly, in some exemplary embodiments, the low-water cleansing composition, having a total surfactant concentration of 10.0 to 60.0 wt. %, based on the total weight of the composition may have a % active surfactant content of 2.5 (10.0 wt. % active surfactant at a dilution of 25% active surfactant) to 60 (60 wt. % active surfactant at a dilution of 100% active surfactant). In some exemplary embodiments, the low-water cleansing composition has a % active surfactant concentration of about 5.0 to about 25% active surfactant, including between about 7.0% and about 20% active surfactant, about 9% and about 18% active surfactant; and at least 10% to about 15% active surfactant.

In certain exemplary embodiments, the low-water cleansing composition includes one or more humectants. Non-limiting examples of humectants include propylene glycol, hexylene glycol, 1,4-dihydroxyhexane, 1,2,6-hexanetriol, sorbitol, butylene glycol, caprylyl glycol, propanediols, such as methyl propane diol, dipropylene glycol, triethylene glycol, glycerin (glycerol), polyethylene glycols, ethoxydiglycol, polyethylene sorbitol, and combinations thereof. Other humectants include glycolic acid, glycolate salts, lactate salts, urea, Jojoba wax PEG-120 esters (commercially available from FloraTech), hydroxyethyl urea, alpha-hydroxy acids, such as lactic acid, sodium pyrrolidone carboxylic acid, hyaluronic acid, chitin, and the like. In one exemplary embodiment, the humectant is a mixture of glycerin, sodium L-pyroglutamate (Sodium PCA), and polyethylene glycol.

Non-limiting examples of polyethylene glycol humectants include PEG-4, PEG-6, PEG-7, PEG-8, PEG-9, PEG-10, PEG-12, PEG-14, PEG-16, PEG-18, PEG-20, PEG-32, PEG-33, PEG-40, PEG-45, PEG-55, PEG-60, PEG-75, PEG-80, PEG-90, PEG-100, PEG-135, PEG-150, PEG-180, PEG-200, PEG-220, PEG-240, and PEG-800.

The humectant, or mixture of humectants, may be included in the low-water cleansing composition in an amount up to about 20.0 wt. %, or up to about 15.0 wt. %, or up to about 12.0 wt. %, or up to about 10.0 wt. %, or up to about 8.0 wt. % or up to about 6.0 wt. %, or up to about 5.0 wt. %. In certain exemplary embodiments, the humectant is included in an amount from about 0.05 wt. %, or from about 1.0 wt. %, or from about 3.5 wt. %, or from about 5.0 wt. %, or from about 6.5 wt. %, or from about 7.0 wt. %, or from about 7.5 wt. %, based upon the total weight of the composition. In one exemplary embodiment, the humectant, or mixture of humectants, is included in an amount from about 0.10 to about 15.0 wt. %, or about 3.0 to about 10.0 wt. %, about 4.0 to about 8.0 wt. %, or from about 5.0 to about 7.5 wt. %, based upon the total weight of the composition.

The low-water cleansing composition of the present disclosure exhibit a pH in the range of from about 2.5 to about 12.0, or a pH in the range of from about 3.5 to about 10, or in the range of from about 4.0 and about 9.5. When necessary, a pH adjusting agent or constituent may be used to provide and/or maintain the pH of a composition. Exemplary pH adjusting agents include, but are not limited to, primary amines, such as monoethanolamine; organic acids, such as citric acid, lactic acid, formic acid, acetic acid, proponic acid, butyric acid, caproic acid, oxalic acid, maleic acid, benzoic acid, carbonic acid, and the like. In certain exemplary embodiments, the low-water cleansing composition includes citric acid. The pH adjusting agent may be included in any amount necessary to sufficiently adjust the pH to a desired level. In some exemplary embodiments, the pH adjusting agent, if present, is included in at least about 0.01 wt. %, or in at least about 0.025 wt. %, or in at least about 0.05 wt. %, or in at least about 0.1 wt. %, or in at least about 0.2 wt. %, based on the total weight of the low-water cleansing composition. In some exemplary embodiments, the pH adjusting agent is included in an amount between 0.01 wt. % and 1.0 wt. %, or between 0.25 wt. % and 0.5 wt. %, or between 0.05 wt. % and 0.2 wt. %, based on the total weight of the low-water cleansing composition.

In one or more embodiments, the low-water cleansing composition includes one or more emollients (also known as a skin conditioner or moisturizer). Non-limiting examples of suitable emollients include aloe, aloe oil, jojoba oil, vitamin E, vitamin E acetate (tocopheryl acetate), Vitamin $B_3$ (niacinamide), $C_{6-10}$ alkane diols, sodium salt of pyroglutamic acid ( ) PEG-7 glyceryl cocoate, coco-glucoside and/or glyceryl oleate (Lamisoft® PO), and polyquaternium, such as polyquaternium 10 and 39.

The emollient can be included in the low-water cleansing composition in an amount from about 0.5 to about 5.0 wt. %, in other embodiments, from about 0.75 to about 3.5 wt. %, or from about 1.0 to about 3.0 wt. %, or from about 1.25 to about 2.5 wt. %, or from about 1.5 to about 2.25 wt. %, based upon the total weight of the composition.

In some exemplary embodiments, the low-water cleansing composition includes less than 3 wt. % of an oil, including less than 2 wt. %, less than 1.5 wt. %, and less than 1.0 wt. %. In some instances, the cleansing composition is substantially (less than 0.5 wt. %) or completely free of oil.

The low-water cleansing composition may further comprise one or more antioxidants, or UV stabilizers, such as, for example, inorganic sulfite salts, including sodium sulfite, potassium sulfite, ammonium sulfite, sodium bisulfite, ammonium bisulfite, sodium metabisulfite and potassium metabisulfite; diethylhexyl syringylidene malonate; Vitamin A and related compounds, Vitamin E and related compounds; Vitamin C and related compounds; diisopropyl vanillidene malonate (also referred to as DIPVM) and related compounds; Tetrahydrocurcumenoids; green tea, white tea, alpha lipoic acid, isoflavones, selenium, zinc, Coenzyme Q10, turmeric, curcumin, butylhydroxy toluene (BHT), ethylenediaminetetraacetic acid (EDTA), ethylenediamine-N,N'-disuccinic acid (EDDS), and other antioxidants commonly used in the art. Amounts of antioxidants to be added to the compositions of the invention are generally between about 0.01% by weight to about 10.0% by weight, preferably between about 0.1% by weight to about 5.0% by weight.

The low-water cleansing composition may further comprise one or more deposition enhancers. A suitable deposition enhancer works unidirectionally and will allow ingredients within the composition to penetrate deeper into the stratum corneum while preventing the loss of materials from the skin. Advantageously, the deposition enhancer provides a cosmetically acceptable skin feel to the formulation.

In one or more embodiments, the deposition enhancers include one or more of surfactants, bile salts and derivatives thereof, chelating agents, and sulphoxides. Some examples of acceptable deposition enhancers include a quaternary ammonium compound, hydroxypropyl methylcellulose, dimethyl sulphoxides (DMSO), DMA, DMF, 1-dodecylazacycloheptan-2-one (azone), pyrrolidones such as 2-Pyrrolidone (2P) and N-Methyl-2-Pyrrolidone (NMP), long-chain fatty acids such as oleic acid and fatty acids with a saturated alkyl chain length of about $C_{10}$-$C_{12}$, essential oils, terpenes, terpenoids, oxazolidinones such as 4-decyloxazolidin-2-one, sodium lauryl sulfate (SLS), sodium laureate, polysorbates, sodium glyacolate, sodium deoxycholate, caprylic acid, EDTA, phospholipids, $C_{12-15}$ Alkyl Benzoate, pentylene glycol, ethoxydiglycol, polysorbate-polyethylenesorbitan-monolaurate, and lecithin. In one or more exemplary embodiments, the deposition enhancer comprises a hydroxy-terminated polyurethane compound chosen from polyolprepolymer-2, polyolprepolymer-14, and polyolprepolymer-15. Polyolprepolymer-2 is sometimes referred to as PPG-12/SMDI copolymer.

In one or more exemplary embodiments, the deposition enhancer is a quaternary ammonium compound such as polyquaternium-6, −7, −10, −22, −37, −39, −74 or −101.

The deposition enhancer may be included in the low-water cleansing composition in an amount from about 0.005 wt. % to about 10.0 wt. %, from about 0.01 wt. % to about 5.0 wt. %, from about 0.05 wt. % to about 3.0 wt. %, from about 0.1 wt. % to about 2.0 wt. %, or from about 0.2 wt. % to about 1.0 wt. %, based upon the total weight of the composition.

Optionally, the low-water cleansing composition may include one or more chelators. Examples of chelators include ethylenediaminetetraacetic acid (EDTA), and ethylenediamine N,N'-disuccinic acid (EDDS), such as trisodium ethylenediamine disuccinate. In one or more embodiments, the amount of chelating agent is from about 0.05 to about 5 wt. %, in other embodiments, from about 0.1 to about 1 wt. %, or from about 0.2 to about 0.5 wt. % based upon the total weight of the cleansing composition.

Although the alcohol in the present composition acts as a preservative, the low-water cleansing composition may further comprise one or more additional preservatives. In other exemplary embodiments, the low-water foamable cleansing composition is free of any preservative other than alcohol. A preservative is a natural or synthetic ingredient that can be added to personal care products to prevent spoilage, such as from microbial growth or undesirable chemical changes. Typical cosmetic preservatives are classified as natural antimicrobials, broad-spectrum preservatives, or stabilizers.

Many different types of preservatives are envisioned as being applicable in the current low-water foamable cleansing composition. Non-limiting examples of preservatives include one or more of isothiazolinones, such as methylchloroisothiazolinone (such as Kathon™ CG) and methylisothiazolinone; parabens including butylparaben, propylparaben, methylparaben and germaben II; phenoxyetyhanol and ethylhexylglycerin, organic acids such as potassium sorbate, sodium benzoate and levulinic acid; and phenoxyethanols.

The preservative can be added in the low-water foamable cleansing composition in an amount up to about 10.0 wt. %, or from about 0.01 wt. % to about 5.0 wt. %, or from about 0.05 wt. % to about 2.0 wt. %, based on the weight of the total composition. In one exemplary embodiment, the preservative is present in an amount from about 0.05 to about 0.15 wt. %, based on the weight of the total composition.

The low-water composition may further comprise one or more anti-irritants. Anti-irritants reduce signs of inflammation on the skin such as swelling, tenderness, pain, itching, or redness. There are three main types of anti-irritants, all of which are envisioned as being applicable in the subject invention: (1) compounds that operate by complexing the irritant itself, (2) compounds that react with the skin to block reactive sites preventing the irritant from reacting directly with the skin, and (3) compounds that prevent physical contact between the skin and irritant.

Certain exemplary examples of suitable anti-irritants include Aloe Vera, allantoin, anion-cation complexes, aryloxypropionates, azulene, carboxymethyl cellulose, cetyl alcohol, diethyl phthalate, Emcol E607, monoethanolamine, glycogen, lanolin, N-(2-Hydroxylthyl) Palmitamide, N-Lauroyl Sarcosinates, Maypon 4C, mineral oils, miranols, Myristyl lactate, polypropylene glycol, polyvinyl pyrrolidone (PVP), tertiary amine oxides, thiodioglycolic acid, and zirconia. In one exemplary embodiment, the anti-irritant is avenanthrmides (Avena Sativa (oat), kernel oil, and glycerin) and niacinamide.

The anti-irritant may be included in the composition in an amount up to about 10.0 wt. %, in other embodiments, from about 0.005 wt. % to about 3.0 wt. %, and in other embodiments, from about 0.01 wt. % to about 1.0 wt. %, based upon the total weight of the composition.

The low-water foamable cleansing composition may further comprise a fragrance. Any scent may be used in the low-water foamable cleansing composition including, but not limited to, any scent classification on a standard fragrance chart, such as floral, oriental, woody, and fresh. Exemplary scents include pomegranate, cinnamon, clove, lavender, peppermint, rosemary, thyme, thieves, lemon, citrus, coconut, apricot, plum, watermelon, ginger and combinations thereof.

The fragrance can be included in the low-water foamable cleansing composition in an amount from about 0.005 wt. % to about 5.0 wt. %, in other embodiments, from about 0.01 wt. % to about 3.0 wt. %, and in other embodiments, from about 0.05 wt. % to about 1.0 wt. %, based upon the total weight of the composition. The fragrance can be any made of any perfume, essential oil, aroma compounds, fixatives, terpenes, solvents, and the like. In certain exemplary embodiments, the essential oils may include, for example, one or more of Limonene, Citrus Aurantium Dulcis (Orange) Peel Oil, Eucalyptus Globulus Leaf Oil, Citrus Grandis (Grapefruit) Peel Oil, Linalool, Litsea Cubeba Fruit Oil, Lavandula Hybrida Oil, Abies Sibirica Oil, Mentha Citrata Leaf Extract, Coriandrum Sativum (Coriander) Fruit Oil, Piper Nigrum (Pepper) Fruit Oil, Vaccinium Angustifolium, Punica Granatum Extract, and Canarium Luzonicum Gum Nonvolatiles.

The low-water cleansing composition may further comprise a wide range of optional ingredients that do not deleteriously affect skin health, aesthetics, or foam quality. The CTFA International Cosmetic Ingredient Dictionary and Handbook, Eleventh Edition 2005, and the 2004 CTFA International Buyer's Guide, both of which are incorporated by reference herein in their entirety, describe a wide variety of non-limiting cosmetic and pharmaceutical ingredients commonly used in the skin care industry, that are suitable for use in the compositions of the present invention. Examples of these functional classes include: abrasives, anti-acne agents, anticaking agents, binders, biological additives, bulking agents, chelating agents, chemical additives; colorants, cosmetic astringents, cosmetic biocides, denaturants, drug astringents, emulsifiers, external analgesics, film formers, fragrance components, opacifying agents, plasticizers, preservatives (sometimes referred to as antimicrobials), propellants, reducing agents, skin bleaching agents, skin protectants, solvents, surfactants, foam boosters, hydrotropes, solubilizing agents, suspending agents (nonsurfactant), sunscreen agents, ultraviolet light absorbers, detackifiers, and viscosity increasing agents (aqueous and nonaqueous). Examples of other functional classes of materials useful herein that are well known to one of ordinary skill in the art include solubilizing agents, sequestrants, keratolytics, topical active ingredients, and the like.

In certain embodiments, the low-water cleansing composition is at least substantially free of dimethicone. By "substantially free" of dimethicone, it is meant that the low-water cleansing composition includes less than 5.0 wt. % of dimethicone, or in some exemplary embodiments, less than 1.0 wt. % of dimethicone, or in some exemplary embodiments, less than 0.05 wt. % dimethicone. In various exemplary embodiments, the low-water foamable cleansing composition is entirely free of dimethicone.

Some exemplary embodiments include dimethicone. In such embodiments, the dimethicone may be included in at least 0.05 wt. %, or at least 0.1 wt. %, or at least 0.5 wt. %, or at least 0.75 wt. %. In some exemplary embodiments, the cleansing composition includes dimethicone in an amount from about 0.1 to 1.0 wt. %, or from 0.5 to 1.0 wt. %.

Examples of dimethicones include silicone glycols, including without limitation dimethicone PEG-7 undecylenate, PEG-10 dimethicone, PEG-8 dimethicone, PEG-12 dimethicone, perfluorononylethyl carboxydecal PEG 10, PEG-20/PPG-23 dimethicone, PEG-11 methyl ether dimethicone, bis-PEG/PPG-20/20 dimethicone, silicone quats, PEG-9 dimethicone, PPG-12 dimethicone, fluoro PEG-8 dimethicone, PEG-23/PPG-6 dimethicone, PEG-20/PPG-23 dimethicone, PEG 17 dimethicone, PEG-5/PPG-3 methicone, bis-PEG-18 methyl ether dimethyl silane, bis-PEG-20 dimethicone, PEG/PPG-20/15 dimethicone copolyol and sulfosuccinate blends, PEG-8 dimethicone\dimmer acid blends, PEG-8 dimethicone\fatty acid blends, PEG-8 dimethicone\cold pressed vegetable oil\polyquaternium blends, random block polymers and mixtures thereof.

The low-water cleansing composition may include one or more thickening agents. Examples of thickening agents include polyurethane-based thickeners, such as steareth-100/PEG-136/HDI copolymer (Rheoluxe® 811); sodium chloride; propylene glycol; PEG-120 methyl glucose dioleate and methyl gluceth-10 (Ritathix DOE, available from Rita Corp.); hydroxyethyl cellulose; quaternized hydroxyethyl cellulose (Polyquaternium-10); Poly(2-methacryloxyethyltrimethylammonium chloride) (Polyquaternium-37); polyquaternium-39; hydroxypropyl cellulose; methyl cellulose; carboxymethyl cellulose; starch polymers; guar hydroxypropyltrimonium chloride; and ammonium acryloyldimethyltaurate/VP copolymer.

In one or more exemplary embodiments, the low-water cleansing composition may include polyacrylate thickening agents such as those conventionally available and/or known in the art. Examples of polyacrylate thickening agents include carbomers, acrylates/C 10-30 alkyl acrylate crosspolymers, copolymers of acrylic acid and alkyl (C5-C 10) acrylate, copolymers of acrylic acid and maleic anhydride, and mixtures thereof. In one or more embodiments, the low-water cleansing composition is in the form of a thickened gel and includes an effective amount of a polymeric thickening agent to adjust the viscosity of the composition to a viscosity range of from about 1000 to about 65,000 centipoise. In some embodiments, the viscosity of the composition is from about 5,000 to about 35,000, and in another embodiment, the viscosity is from about 10,000 to about 25,000. The viscosity is measured by a Brookfield RV Viscometer using RV and/or LV Spindles at 22° C. +/−3° C.

As will be appreciated by one of skill in the art, the effective amount of thickening agent will vary depending upon a number of factors, including the amount of other ingredients in the low-water composition. In one or more embodiments, an effective amount of thickening agent is at least about 0.01 wt. %, based upon the total weight of the composition. In other embodiments, the effective amount is at least about 0.02 wt. %, or at least about 0.05 wt. %, or at least about 0.1 wt. %. In certain exemplary embodiments, the effective amount of thickening agent is at least about 0.5 wt. %, or at least about 0.75 wt. %, based upon the total weight of the composition. In one or more embodiments, the compositions according to the present invention comprise up to about 10% by weight of the total composition of a thickening agent. In certain embodiments, the amount of thickening agent is from about 0.01 to about 1.0 wt. %, or from about 0.02 to about 0.4 wt. %, or from about 0.05 to about 0.3 wt. %, based upon the total weight of the composition. The amount of thickening agent may be from about 0.1 to about 10.0 wt. %, or from about 0.5 to about 5.0 wt. %, or from about 0.75 to about 2.0 wt. %, based upon the total weight of the composition.

Optionally, the low-water cleansing composition may include one or more pharmacological agents, with the proviso that the pharmacological ingredient does not deleteriously affect the properties of the composition. Examples of such agents include, but are not limited to, antifungal agents, antiviral agents, antimicrobial agents, and antiparasitic agents. In one or more embodiments, one or more antimicrobial agents are included. Examples of antimicrobial agents include, but are not limited to, triclosan, also known as 5-chloro-2(2,4-dichlorophenoxy) phenol (PCMX) and available from Ciba-Geigy Corporation under the tradename IRGASAN®; chloroxylenol, also known as 4-chloro-3,5-xylenol, available from Nipa Laboratories, Inc. under the tradenames NIPACIDE® MX or PX; hexetidine, also known as 5-amino-1,3-bis(2-ethylhexyl)-5-methyl-hexahydropyrimidine; chlorhexidine salts including chlorhexidine gluconate and the salts of N,N"-Bis(4-chlorophenyl)-3,12-diimino-2,4,11,14-tetraazatetradecanediimidiamide; 2-bromo-2-nitropropane-1; 3-diol, benzalkonium chloride; cetylpyridinium chloride; alkylbenzyldimethylammonium chlorides; iodine; phenol, bisphenol, diphenyl ether, phenol derivatives, povidone-iodine including polyvinylpyrrolidinone-iodine; parabens; hydantoins and derivatives thereof, including 2,4-imidazolidinedione and derivatives of 2,4-imidazolidinedione as well as dimethylol-5,5-dimethylhydantoin (also known as DMDM hydantoin or glydant); phenoxyethanol; cis isomer of 1-(3-chloroallyl)-3,5,6-triaza-1-azoniaadamantane chloride, also known as quatemium-15 and available from Dow Chemical Company under the tradename DOWCIL™ 200; diazolidinyl urea; benzethonium chloride; methylbenzethonium chloride; glyceryl laurate, transition metal compounds such as silver, copper, magnesium, zinc compounds, hydrogen peroxide, chlorine dioxide, anilides, bisguanidines, a blend of biostatic and fungistatic agents having the INCI name caprylhydroxamic acid (and) propanediol, and mixtures thereof.

Accordingly, the low-water cleansing composition may be formulated as an antimicrobial, antiviral, antibacterial, and/or antifungal composition. Such compositions are capable of achieving an antimicrobial log reduction of at least 2.5 log.

In one or more embodiments, the composition comprises from about 0.05 to about 3 wt. %, in other embodiments, from about 0.07 to about 2.5 wt. %, in other embodiments, from about 0.09 to about 1 wt. %, in other embodiments, from about 0.1 to about 0.75 wt. %, in other embodiments, from about 0.15 to about 0.5 wt. of at least one antimicrobial agents, based upon the total weight of the composition.

Alternatively, various exemplary embodiments of the present application are directed to a non-antimicrobial, non-antibacterial, non-antiviral, and/or non-antifungal composition. Such compositions achieve an antimicrobial log reduction in use no greater than 3.0 log, including no greater than 2.5 log, no greater than 2.0 log, and no greater than 1.5 log. In some exemplary embodiments, the non-antimicrobial composition achieves an antimicrobial kill less than 1.0 log.

In one or more embodiments, compositions of the present invention may further include one or more probiotics and/or prebiotics. In one or more embodiments, the one or more probiotics include one or more skin commensal microorganisms which positively affect the skin microbiota. For example, the one or more probiotics can include microorganisms that positively affect the skin surface environment, e.g., by altering the pH or inhibiting growth of pathogenic microorganisms. In one or more embodiments, the one or more probiotics can include one or more microorganisms naturally found on the skin surface of the individual. In one or more embodiments, the one or more probiotics can include one or more microorganism that are not naturally found on the skin surface of the individual, but positively affect the skin surface environment. In one or more embodiments, the one or more probiotics can include one or more engineered microorganisms. For example, the one or more probiotics can include a microorganism genetically engineered to have a property that positively affects the skin surface environment, e.g., by synthesizing and excreting an inhibitor of pathogenic microorganisms. See e.g., Martin et al. (2013) Microbial Cell Factories, 12:71, which is incorporated herein by reference. In one or more embodiments, the probiotic comprises live probiotic microorganisms. In one or more embodiments, the probiotics may be included in a live form, dead form, semi-active or in deactivated form and fragments or fractions originating from the microorganism either live or dead (e.g., as a lyophilized powder). In one or more embodiments, the probiotic includes culture supernatants of the microorganisms.

In one or more embodiments, the one or more probiotics include one or more bacterial probiotics. In one or more embodiments, the one or more bacterial probiotics include one or more of *Firmicutes, Actinobacteria, Bacteriodetes, Proteobacteria*, or *Cyanobacteria*. In one or more embodiments, the one or more bacterial probiotics include one or more of *Corynebacteria, Propionibacteria, Micrococci*, or *Staphylococci*. In one or more embodiments, the one or more bacterial probiotics include non-lactic acid and/or lactic acid producing bacteria (LAB) and can include *Bacteroides, Bifdobacterium*, and *Lactobacillus*. In one or more embodiments, the one or more bacterial probiotics include certain strains of *Aerococcus, E. coli, Bacillus, Enterococcus, Fusobacterium, Lactococcus, Leuconostoc, Melissacoccus, Micrococcus, Oenococcus, Sporolactobacillus, Streptococcus, Staphylococcus, Saccharomyces, Pediococcus, Peptostreptococcus, Proprionebacterium*, and *Weissella*. A wide variety of strains of bacteria are available from the ATCC, Manassas, Va. In one or more embodiments, the one or more probiotics include one or more non-pathogenic strains of pathogenic bacteria.

In one or more embodiments, the one or more treatment agents include one or more prebiotics. In one or more embodiments, the one or more prebiotics are agents that promote the survival and/or growth of microorganisms of interest on the skin surface of the individual. In one or more embodiments, the one or more prebiotics include at least one of gal acto-oligosaccharides, fructo-oligosaccharides, inulin, or lactulose. In one or more embodiments, the one or more prebiotics include one or more of iron, biotin, nicotinic acid, D-pantothenic acid, pyridoxal, pyridoxamine dihydrochloride, thiamin hydrochloride, valine, arginine, galactose, mannose, fructose, sucrose, lactose, or maltose. In one or more embodiments, the one or more prebiotics include one or more of plant derived prebiotics, e.g., derived from acacia gum, konjac, chicory root, Jerusalem artichoke, asparagus, and dandelion greens. See e.g., U.S. Patent Application Publication NO. 2013/0115317 A1; and Bateni et al. (2013) Am. J. Dermatology Venereology 2:10-14, both of which are incorporated herein by reference.

The composition may further comprise a wide range of optional ingredients that do not deleteriously affect skin health, aesthetics, or foam quality. The CTFA International Cosmetic Ingredient Dictionary and Handbook, Eleventh Edition 2005, and the 2004 CTFA International Buyer's Guide, both of which are incorporated by reference herein in their entirety, describe a wide variety of non-limiting cosmetic and pharmaceutical ingredients commonly used in the skin care industry, that are suitable for use in the compositions of the present invention. Examples of these functional classes include: abrasives, anti-acne agents, anticaking agents, antioxidants, binders, biological additives, bulking agents, chelating agents, chemical additives; colorants, cosmetic astringents, cosmetic biocides, denaturants, drug astringents, emulsifiers, external analgesics, film formers, fragrance components, opacifying agents, plasticizers, preservatives (sometimes referred to as antimicrobials), propellants, reducing agents, skin bleaching agents, skin-conditioning agents (emollient, miscellaneous, and occlusive), skin protectants, solvents, surfactants, foam boosters, hydrotropes, solubilizing agents, suspending agents (nonsurfactant), sunscreen agents, ultraviolet light absorbers, detackifiers, and viscosity increasing agents (aqueous and nonaqueous). Examples of other functional classes of materials useful herein that are well known to one of ordinary skill in the art include solubilizing agents, sequestrants, keratolytics, topical active ingredients, and the like.

The compositions of the present invention may be employed in many types of dispensers typically used for soaps, sanitizers, or lotion products, for example pump dispensers. In some embodiments, when delivering a concentrate product, the pump volumes may need to be adjusted to deliver lower volumes of liquid and/or higher volumes of air (when dispensing foam). A wide variety of pump dispensers are suitable. Pump dispensers may be affixed to bottles or other free-standing containers. Pump dispensers may be incorporated into wall-mounted dispensers. Pump dispensers may be activated manually by hand or foot pump, or may be automatically activated. Useful dispensers include those available from GOJO Industries under the designations NXT® and TFX™ as well as traditional bag-in-box dispensers. Examples of dispensers are described in U.S. Pat. Nos. 5,265,772, 5,944,227, 6,877,642, 7,028,861, 7,611,030, and 7,621,426, all of which are incorporated herein by reference. In one or more embodiments, the dispenser includes an outlet such as a nozzle, through which the composition is dispensed. In certain exemplary embodiments, the low-water composition is used in dispensers that employ foaming pumps, which combine ambient air or an inert gas and the composition in a mixing chamber and pass the mixture through a mesh screen. Exemplary embodiments of foam pumps that may be used are shown and described in, U.S. Pat. No. 7,303,099 titled Stepped Pump Foam Dispenser; U.S. Pat. No. 8,002,150 titled Split Engagement Flange for Soap Piston; U.S. Pat. No. 8,091,739 titled Engagement Flange for Fluid Dispenser Pump Piston; U.S. Pat. No. 8,113,388 titled Engagement Flange for Removable Dispenser Cartridge; U.S. Pat. No. 8,272,539, Angled Slot Foam Dispenser; U.S. U.S. 8,272,540 titled Split Engagement Flange for Soap Dispenser Pump Piston; U.S. Pat. No. 8,464,912 titled Split Engagement Flange for Soap Dispenser Pump Piston; U.S. Pat. No. 8,360,286 titled Draw Back Push Pump; U.S. patent application Ser. No. 15/429,389 titled High Quality Non-Aerosol Hand Sanitizing Foam; U.S. patent application Ser. No. 15/369,007 Sequentially Activated Multi-Diaphragm Foam Pumps, Refill Units and Dispenser Systems; U.S. Pat. No. 8,172,555 titled Diaphragm Foam Pump; U.S. 2008/0,277,421 titled Gear Pump and Foam Dispenser, all of which are incorporated herein by reference in their entirety.

Exemplary touch-fee dispensers are also shown and described in U.S. Pat. No. 7,837,066 titled Electronically Keyed Dispensing System And Related Methods Utilizing Near Field Response; U.S. Pat. No. 9,172,266 title Power Systems For Touch Free Dispensers and Refill Units Containing a Power Source; U.S. Pat. No. 7,909,209 titled Apparatus for Hands-Free Dispensing of a Measured Quantity of Material; U.S. Pat. No. 7,611,030 titled Apparatus for Hands-Free Dispensing of a Measured Quantity of Material; U.S. Pat. No. 7,621,426 titled Electronically Keyed Dispensing Systems and Related Methods Utilizing Near Field Response; and U.S. Pat. Pub. No. 8/960,498 titled Touch-Free Dispenser with Single Cell Operation and Battery Banking; all which are incorporated herein by reference.

Exemplary dispensers and pumps that are particularly suitable for dispensing the compositions disclosed herein in the form of foam may be found in U.S. patent application Ser. No. 15/356,795 titled Foam Dispensing Systems, Pumps and Refill Units Having High Air to Liquid Ratios, and U.S. patent application Ser. No. 15/480,711 titled Sequentially Activated Multi-Diaphragm Foam Pumps, Refill Units and Dispenser Systems, which are incorporated herein by reference in their entirety.

A surprising benefit of the present low-water cleansing composition is that even with the presence of alcohol, the composition does not negatively impact skin's water content after use, as measured by the transepidermal water loss measurement. In some exemplary embodiments, after application to a skin surface, the low-water cleansing composition produces a transepidermal water loss measurement that is not higher by a statistically significant amount, compared to an otherwise identical composition that does not include alcohol.

Another benefit of the present low-water cleansing composition is that even with the presence of alcohol, the composition improves skin's overall hydration after use, as measured using a Corneometer®. In some exemplary embodiments, the low-water cleansing composition produces a hydration level that is not lower by a statistically significant amount, compared to an otherwise identical composition that does not include alcohol.

In some exemplary embodiments, the low-water cleansing composition includes the following ingredients:

TABLE 1

| Ingredient | Wt. % of the total Composition |
|---|---|
| $C_1$-$C_8$ Alcohol | 5.0-40.0 |
| Total Surfactant | 10.0-40.0 |
| Humectant | 0.1-10.0 |
| Emollient | 0-3.0 |
| pH adjuster | 0.01-1.0 |
| Thickener/emulsifier | 0-2.0 |
| Water | q.s. |
| Active surfactant | >5.0 |

TABLE 2

| Ingredient | Wt. % of the total Composition |
|---|---|
| $C_1$-$C_8$ Alcohol | 15.0-30.0 |
| Primary Surfactant | 10.0-25.0 |
| Secondary Surfactant | 2.0-20.0 |
| Humectant | 2.0-8.0 |
| Emollient | 0.5-2.0 |
| pH adjuster | 0.05-0.5 |
| Thickener/emulsifier | 0.1-1.0 |
| Water | q.s. |
| Active surfactant | >7.0 |

TABLE 3

| Ingredient | Wt. % of the total Composition |
|---|---|
| $C_{1-8}$ Alcohol | 5.0-20.0 |
| Primary Surfactant | 12.0-20.0 |
| Secondary Surfactant | 4.0-15.0 |
| Humectant(s) | 5.0-20.0 |
| Emollient | 2.0-6.0 |
| Antimicrobial | 0.5-5.0 |
| pH adjuster | 0.01-1.0 |
| Water | q.s. |
| Active surfactant | >10.0 |

TABLE 4

| Ingredient | Wt. % Active Surfactant |
|---|---|
| $C_{1-8}$ Alcohol | 5.0-40.0 |
| Active Surfactant | 5.0-25.0% |

TABLE 5

| Ingredient | Wt. % Active |
|---|---|
| $C_{1-8}$ Alcohol | 5.0-30.0 |
| Active Surfactant | 7.0-20.0% |

Further exemplary embodiments relate to a method of skin treatment with a foamable cleansing composition. In certain exemplary embodiments, the method includes applying a low-water cleansing composition to a skin surface. In certain exemplary embodiments, the low-water cleansing composition includes from about 10 to about 40 wt. % of one or more $C_1$-$C_8$ alcohols based on the total weight of the composition; greater than about 10 wt. % of one or more surfactants; and water.

EXAMPLES

The following examples are included for purposes of illustration and are not intended to limit the scope of the disclosure described herein.

Example 1

Foam Quality

The impact that the addition of alcohol has on a low-water cleansing composition was tested by measuring the foam volume and density of various compositions that were concentrated anywhere from 2× to 5×. To measure foam volume, an electronic hands-free dispenser was used to actuate a pump at a controlled speed and distance. The foam density was measured by first priming the dispenser until 5 outputs of soap were delivered. Six actuations were then collected into a tared, graduated, 100 mL flask. The weight of the fluid and the foam volume was then recorded. The results are illustrated in FIG. 1. The compositions tested included various amounts of alcohol (0%-30%). Surprisingly, as the amount of alcohol increased, the volume increased as well, with the 2× low-water cleansing composition with 30% alcohol having the greatest foam volume.

Figure 2:
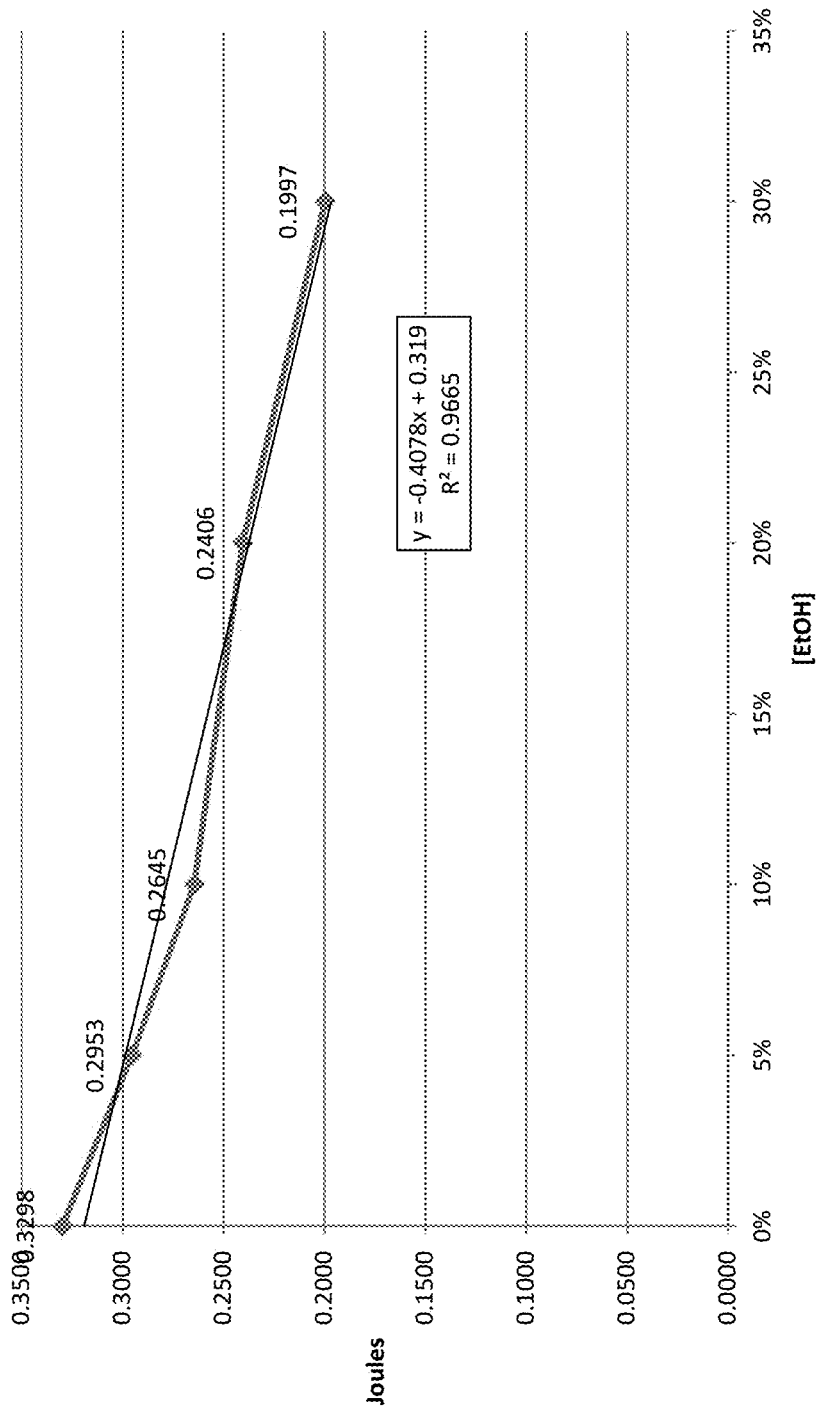
FIG. 2 graphically illustrates the energy usage to deliver low-water cleansing compositions including various levels of ethanol.
Figure 3:
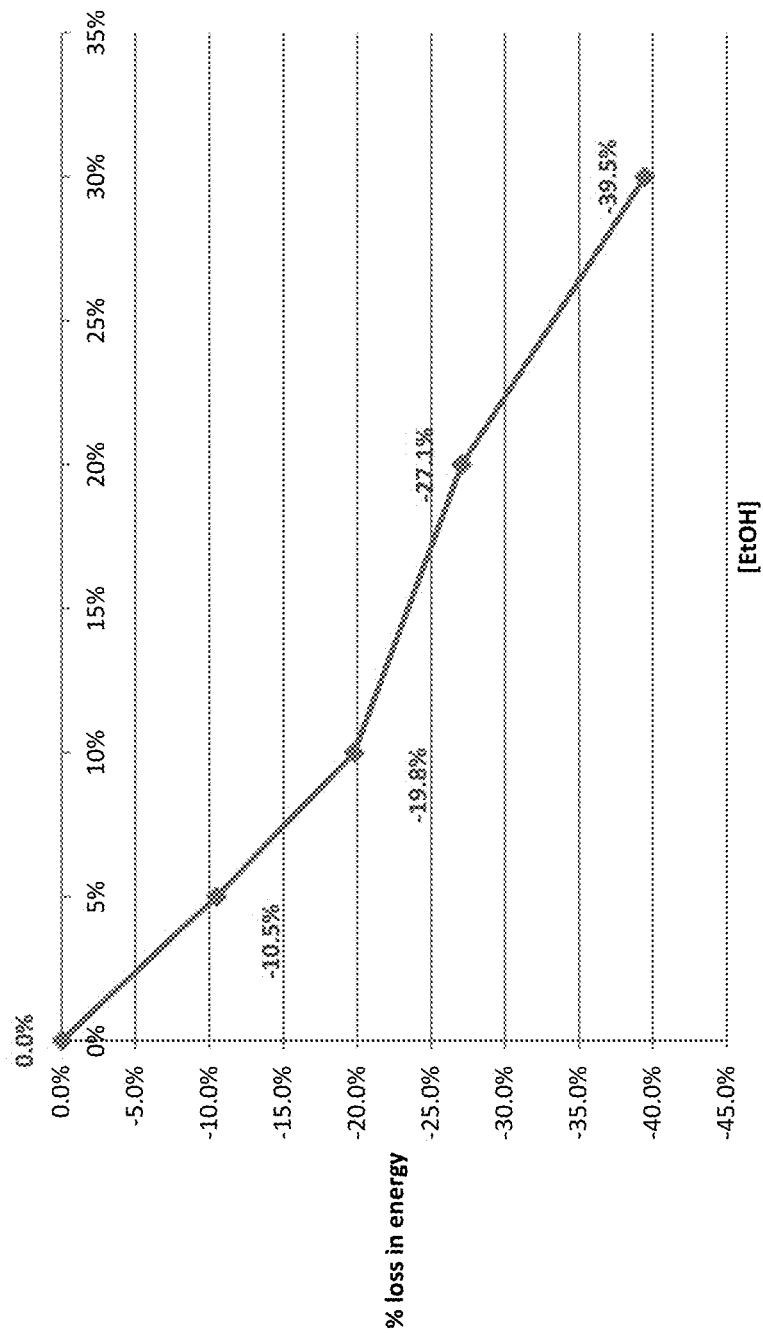
FIG. 3 graphically illustrates the reduction in energy required to deliver low-water cleansing compositions including various levels of ethanol.

A foam generator was used to compare the energy required to dispense foam of different formulations. As illustrated in FIG. 2, the amount of energy required to operate a pump to dispense a low-water cleansing composition decreased with increasing alcohol concentration. Notably, a low-water cleansing composition incorporating 30 wt. % ethanol required 0.1997 Joules of energy, while an otherwise identical low-water cleansing composition required 0.3298 Joules of energy. This can also be illustrated as a reduction in work required to operate a pump (FIG. 3). As shown in FIG. 3, a low-water cleansing composition with 30% ethanol required 39.5% less energy than an otherwise identical low-water cleansing composition that was free of ethanol.

Example 2

Foam Density

Figure 4:
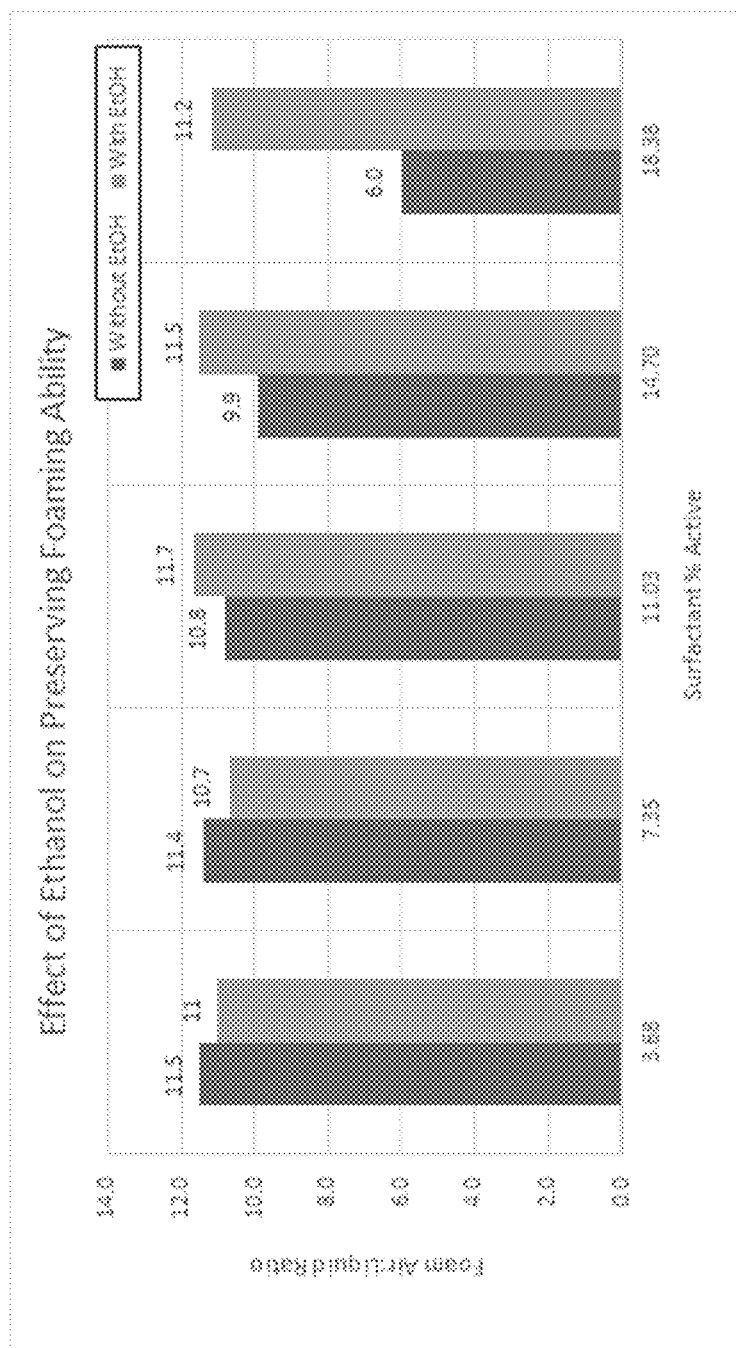
FIG. 4 graphically illustrates the effect of alcohol on preserving the foaming ability of compositions.

The effect of alcohol on the foamability of cleansing compositions at increasing active surfactant levels was tested and the results are illustrated in FIG. 4. Compositions formulated in accordance with the present application with 20 wt. % ethanol were prepared using varied levels of active surfactant (3.68 wt. %, 7.35 wt. %, 11.08 wt. %, 14.70 wt. %, and 18.38 wt. %). Similar compositions were prepared at the same surfactant active levels, only the ethanol was replaced with water. The compositions were dispensed through a foam dispenser and the output foam volume was measured. As the fluid volume was known, the total air volume was calculated by subtracting the fluid volume from the total foam volume. FIG. 4 illustrates the foam air volume/liquid volume ratios for each composition. As shown in FIG. 4, as the percent active surfactant level increases in the alcohol-free compositions, the air volume to liquid volume ratio decreases, which indicates that the compositions foaming ability is also decreasing. However, it has been surprisingly discovered that the alcohol-containing compositions (here with 20% ethanol) demonstrated consistent foaming ability, even as the percent active surfactant levels were raised to 18.38 wt. %.

Additionally, as both the level of surfactant and level of alcohol affect the density of the composition, comparing foams created with different density solutions may not accurately portray the density of the foam. Thus, although density is typically measured in mass/volume, the foam density may be converted to a fluid fraction type metric by converting the fluid mass to fluid volume: $mL_{FLUID}/mL_{FOAM}$. In some exemplary embodiments, the low-water foamable composition achieves a foam density, as dispensed, of 0.1 $mL_{FLUID}/mL_{FOAM}$ or less, including 0.1 $mL_{FLUID}/mL_{FOAM}$ or less, and 0.05 $mL_{FLUID}/mL_{FOAM}$ or less.

In some exemplary embodiments, the low-water cleansing compositions having an active surfactant level of at least 5.0% achieve a foam air volume to liquid volume ratio above 11. In some exemplary embodiments, the low-water cleansing compositions having an active surfactant level of at least 7.0% achieve a foam air volume to liquid volume ratio above 11.

Example 3

Foamable Composition Viscosity

Figure 5:
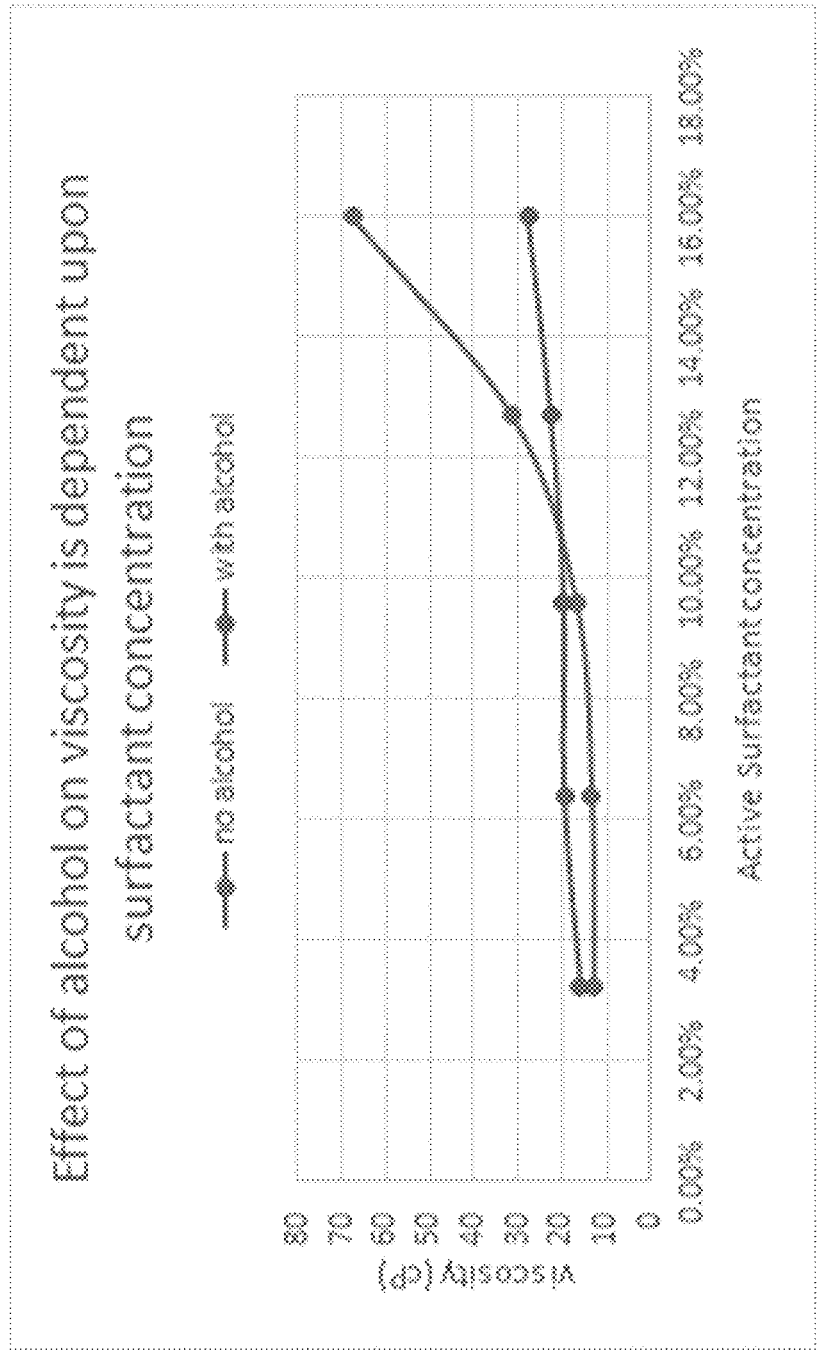
FIG. 5 graphically illustrates the effect of alcohol on the viscosity of compositions at various active surfactant concentrations.

The viscosity of the foamable low-water cleansing compositions with 20 wt. % ethanol was measured at various levels of active surfactant concentration and compared to the viscosity of similar cleansing compositions in which the ethanol was replaced with water. As illustrated in FIG. 5, at active surfactant concentrations between 3.0% and 16.0%, the foamable low-water cleansing composition maintained viscosity levels below 30 cPs. In fact, at active surfactant levels at or below 13%, the foamable low-water cleansing composition maintained viscosity levels below 25 cPs. In contrast, the alcohol-free composition demonstrated an increase in viscosity to over 30 cPs at an active surfactant level of about 13%.

In some exemplary embodiments, the foamable cleansing composition has a viscosity of 50 cPs or below at active surfactant levels between 5% and 30%, including a viscosity of 40 cPs or below at active surfactant levels between 5% and 25%.

Although embodiments of the invention have been described herein, it should be appreciated that many modifications can be made without departing from the spirit and scope of the general inventive concepts. All such modifications are intended to be included within the scope of the invention.

The invention claimed is:

1. A low-water cleansing composition comprising:
   from greater than 15 wt. % to less than 30 wt. % of one or more C1-C8 alcohols;
   at least 16 wt. % of a mixture of two or more surfactants, wherein the mixture of surfactants comprises one or more anionic surfactants and one or more zwitterionic surfactants;
   one or more thickening agents; at least 0.05 wt. % of a pH adjuster; and
   water, the wt. % being based on a total weight of the low-water cleansing composition,
   wherein the low-water cleansing composition is a non-antimicrobial cleansing composition, and
   wherein the low-water, non-antimicrobial cleansing composition comprises greater than 7.0% active surfactant.

2. The low-water, non-antimicrobial cleansing composition of claim 1, wherein the one or more C1-C8 alcohols are selected from the group consisting of methanol, ethanol, isopropanol, butanol, pentanol, hexanol, and isomers and mixtures thereof.

3. The low-water, non-antimicrobial cleansing composition of claim 1, wherein the one or more C1-C8 alcohols include at least one of ethanol and isopropanol.

4. The low-water, non-antimicrobial cleansing composition of claim 1, wherein the composition includes at least 10 wt. % active surfactant.

5. The low-water, non-antimicrobial cleansing composition of claim 1, wherein the one or more anionic surfactants are selected from the group consisting of sodium alkyl sulfate, sodium dodecyl sulfate, sodium dodecylbenzene sulfonate, sodium laurate, sodium laureth sulfate, sodium lauryl sarcosinate, potassium lauryl sulfate, ammonium lauryl sulfate, ammonium laureth sulfate, ammonium xylene sulfonate, magnesium laureth sulfate, sodium myreth sulfate, sodium nonanoyloxybenzenesulfonate, carboxylates, sulphated esters, sulphated alkanolamides, alkylphenols, and mixtures thereof.

6. The low-water, non-antimicrobial cleansing composition of claim 1, wherein the one or more zwitterionic surfactants are selected from the group consisting of betaines, sultaines, amphoacetates, and amphodiacetates.

7. The low-water, non-antimicrobial cleansing composition of claim 1, further comprising a humectant selected from the group consisting of propylene glycol, hexylene glycol, 1,4-dihydroxyhexane, 1,2,6-hexanetriol, sorbitol, butylene glycol, caprylyl glycol, methyl propane diol, dipropylene glycol, triethylene glycol, glycerin (glycerol), polyethylene glycol, ethoxydiglycol, polyethylene sorbitol, and combinations thereof.

8. The low-water, non-antimicrobial cleansing composition of claim 1, wherein the composition is substantially free of dimethicone.

9. The low-water, non-antimicrobial cleansing composition of claim 1, wherein the composition is in the form of a foamable solution.

10. The low-water, non-antimicrobial cleansing composition of claim 9, wherein the foamable solution generates a foam volume that is at least 30% greater than the foam volume of an otherwise identical low-water, non-antimicrobial cleansing composition that does not include the claimed concentration of alcohol.

11. A method of cleansing a surface comprising:
applying the low-water, non-antimicrobial cleansing composition of claim 1 to a surface.

12. The method of claim 11, wherein the low-water, non-antimicrobial cleansing composition is applied without mixing with additional water.

* * * * *